(12) United States Patent
Markle

(10) Patent No.: US 6,815,235 B1
(45) Date of Patent: Nov. 9, 2004

(54) METHODS OF CONTROLLING FORMATION OF METAL SILICIDE REGIONS, AND SYSTEM FOR PERFORMING SAME

(75) Inventor: Richard J. Markle, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 113 days.

(21) Appl. No.: 10/304,114

(22) Filed: Nov. 25, 2002

(51) Int. Cl.$^7$ .......................... H01L 31/26; H01L 21/76; G01J 5/00

(52) U.S. Cl. ............................ 438/16; 438/14; 438/649; 438/651; 438/755; 374/126; 374/128; 374/178

(58) Field of Search .......................... 438/649, 651, 438/655, 754–755, 757, 14, 16; 374/126, 128, 178

(56) References Cited

U.S. PATENT DOCUMENTS

| | | | |
|---|---|---|---|
| 3,912,559 A | 10/1975 | Harigaya et al. | 148/187 |
| 4,107,835 A | 8/1978 | Bindell et al. | 29/590 |
| 4,897,368 A | 1/1990 | Kobushi et al. | 437/200 |
| 5,034,348 A | 7/1991 | Hartswick et al. | 437/200 |
| 5,248,892 A | 9/1993 | Van Roozendaal et al. | 257/357 |
| 5,316,977 A | 5/1994 | Kunishima et al. | 437/200 |

(List continued on next page.)

FOREIGN PATENT DOCUMENTS

| | | | |
|---|---|---|---|
| DE | 19520782 A1 | 12/1995 | ............ H01L/29/43 |
| DE | 19819438 A1 | 3/1999 | ....... H01L/21/8234 |
| DE | 19750340 A1 | 6/1999 | ......... H01L/27/092 |
| DE | 19952177 A1 | 5/2000 | ......... H01L/21/768 |
| DE | 19940758 A1 | 3/2001 | ......... H01L/21/336 |
| EP | 0 199 939 A2 | 12/1986 | ......... H01L/21/285 |
| EP | 0 417 522 A2 | 3/1991 | ......... H01L/21/285 |
| EP | 0 727 815 A1 | 9/1996 | ............ H01L/21/28 |
| JP | 05055251 A | 3/1993 | ......... H01L/21/336 |
| JP | 11-40679 | 2/1999 | ....... H01L/21/8238 |
| JP | 2002025940 A | 1/2002 | ............ H01L/21/28 |
| WO | WO 95/15005 | 6/1995 | ......... H01L/21/285 |
| WO | WO 96/13061 | 5/1996 | ......... H01L/21/283 |
| WO | WO02/065523 A1 | 8/2002 | ............ H01L/21/28 |

OTHER PUBLICATIONS

Application Ser. No. 10/259,016, entitled "Semiconductor Device Having Different Metal–Semiconductor Portions Formed in a Semiconductor Region and a Method for Fabricating the Semiconductor Device," filed Sep. 27, 2002.

Application Ser. No. 10/260,926, entitled "Semiconductor Device Having Different Metal Silicide Portions and Method for Fabricating the Semiconductor Device," filed Sep. 30, 2002.

Application Ser. No. 10/282,720, entitled "Method of Forming Different Silicide Portions on Different Silicon–Containing Regions in a Semiconductor Device," filed Oct. 29, 2002.

*Primary Examiner*—Donghee Kang
(74) *Attorney, Agent, or Firm*—Williams, Morgan & Amerson, P.C.

(57) ABSTRACT

The present invention is generally directed to various methods of controlling the formation of metal silicide regions, and a system for performing same. In one illustrative embodiment, the method comprises forming a layer of refractory metal above a feature, performing at least one anneal process to convert a portion of the layer of refractory metal to at least one metal silicide region on the feature, and measuring at least one characteristic of at least one metal silicide region while the anneal process is being performed. In another illustrative embodiment, the method comprises forming a layer of refractory metal above a feature, performing at least one anneal process to convert a portion of the layer of refractory metal to at least one metal silicide region on the feature, and performing at least one scatterometric measurement of the metal silicide region after at least a portion of the anneal process is performed to determine at least one characteristic of the metal silicide region.

90 Claims, 5 Drawing Sheets

U.S. PATENT DOCUMENTS

| | | | |
|---|---|---|---|
| 5,317,187 A | 5/1994 | Hindman et al. | 257/659 |
| 5,352,631 A | 10/1994 | Sitaram et al. | 437/200 |
| 5,447,875 A | 9/1995 | Moslehi | 437/41 |
| 5,451,545 A | 9/1995 | Ramaswami et al. | 437/200 |
| 5,565,708 A | 10/1996 | Ohsaki et al. | 257/764 |
| 5,738,917 A | 4/1998 | Besser et al. | 437/576 |
| 5,851,891 A | 12/1998 | Dawson et al. | 438/305 |
| 5,874,342 A | 2/1999 | Tsai et al. | 438/301 |
| 5,899,720 A | 5/1999 | Mikagi | 438/303 |
| 5,902,129 A | 5/1999 | Yoshikawa et al. | 438/592 |
| 5,908,309 A | 6/1999 | Andoh | 438/231 |
| 5,937,325 A | 8/1999 | Ishida | 438/655 |
| 5,998,252 A | 12/1999 | Huang | 438/241 |
| 6,020,242 A | 2/2000 | Tsai et al. | 438/279 |
| 6,040,606 A | 3/2000 | Blair | 257/384 |
| 6,063,681 A | 5/2000 | Son | 438/303 |
| 6,072,222 A | 6/2000 | Nistler | 257/383 |
| 6,100,173 A | 8/2000 | Gardner et al. | 438/592 |
| 6,103,610 A | 8/2000 | Blair | 438/592 |
| 6,132,081 A * | 10/2000 | Han | 374/1 |
| 6,133,130 A | 10/2000 | Lin et al. | 438/586 |
| 6,136,705 A | 10/2000 | Blair | 438/682 |
| 6,177,319 B1 | 1/2001 | Chen | 438/275 |
| 6,187,617 B1 | 2/2001 | Gauthier, Jr. et al. | 438/197 |
| 6,204,103 B1 | 3/2001 | Bai et al. | 438/224 |
| 6,232,227 B1 | 5/2001 | Mikagi | 438/655 |
| 6,238,984 B1 | 5/2001 | Yang | 438/275 |
| 6,238,986 B1 | 5/2001 | Kepler et al. | 438/301 |
| 6,261,898 B1 | 7/2001 | Wu | 438/241 |
| 6,268,255 B1 | 7/2001 | Besser et al. | 438/303 |
| 6,268,257 B1 | 7/2001 | Wieczorek et al. | 438/305 |
| 6,281,067 B1 | 8/2001 | Chien et al. | 438/241 |
| 6,297,135 B1 | 10/2001 | Talwar et al. | 438/592 |
| 6,306,698 B1 | 10/2001 | Wieczorek et al. | 438/197 |
| 6,383,878 B1 | 5/2002 | Huang | 438/299 |
| 6,383,906 B1 | 5/2002 | Wieczorek et al. | 438/592 |
| 6,391,704 B1 | 5/2002 | Hong et al. | 438/241 |
| 6,403,423 B1 | 6/2002 | Weybright et al. | 438/279 |
| 6,451,679 B1 | 9/2002 | Hu et al. | 438/592 |
| 6,468,904 B1 | 10/2002 | Chen et al. | 438/682 |
| 6,528,401 B2 | 3/2003 | Bae et al. | 438/592 |
| 6,528,422 B1 | 3/2003 | Huang et al. | 438/683 |
| 6,531,724 B1 | 3/2003 | Furukawa et al. | 257/288 |
| 6,534,402 B1 | 3/2003 | Liao | 438/659 |
| 6,544,876 B1 | 4/2003 | Iyer | 438/592 |

* cited by examiner

METHODS OF CONTROLLING FORMATION OF METAL SILICIDE REGIONS, AND SYSTEM FOR PERFORMING SAME

BACKGROUND OF THE INVENTION

1. Field of the Invention

This invention relates generally to semiconductor fabrication technology, and, more particularly, to various methods of controlling the formation of metal silicide regions, and a system for performing same.

2. Description of the Related Art

There is a constant drive within the semiconductor industry to increase the operating performance of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors. Moreover, the density of such transistors on a wafer per unit area has dramatically increased as a result of, among other things, the reduction in feature sizes, and an overall desire to minimize the size of various integrated circuit products.

By way of background, modern integrated circuit devices, e.g., microprocessors. ASICs, memory devices, etc., are comprised of millions of field effect transistors formed on a semiconducting substrate, such as silicon. The substrate may be doped with either N-type or P-type dopant materials. An illustrative field effect transistor 10, as shown in FIG. 1, may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit product is comprised of a plurality of conductive interconnections, such as conductive lines and conductive contacts or vias, positioned in multiple layers of insulating material formed above the substrate. These conductive interconnections allow electrical signals to propagate between the transistors formed above the substrate.

The gate electrode 14 has a critical dimension 12, i.e., gate length, that approximately corresponds to the channel length 13 of the device when the transistor 10 is operational. Thus, it is very important that the critical dimension 12 of the gate electrode 14 be formed very accurately. Even small errors in the critical dimension 12 of the gate electrode 14 can result in the failure of the finished product to meet certain target electrical performance characteristics, e.g., switching speed, leakage current, etc. Of course, the critical dimension 12 of the gate electrode 14 is but one example of a feature that must be formed very accurately in modem semiconductor manufacturing operations. Other examples include, but are not limited to, conductive lines, openings in insulating layers to allow subsequent formation of a conductive interconnection, i.e., a conductive line or contact, therein, etc.

Also depicted in FIG. 1 are a plurality of metal silicide regions 17 that are formed above the gate electrode 14 and the source/drain regions 22. In general, one purpose of the metal silicide regions 17 is to reduce contact resistance and thereby enhance various operating characteristics of the transistor 10 and integrated circuit products, e.g., microprocessors, incorporating such transistors 10. The metal silicide regions 17 may be comprised of a variety of different materials, e.g., cobalt silicide, titanium silicide, nickel silicide, platinum silicide, tantalum silicide, tungsten silicide, etc.

The metal silicide regions 17 may be formed by a variety of known techniques. One illustrative process flow for forming the metal silicide regions 17 is depicted in FIGS. 2A–2C. Initially, as shown in FIG. 2A, a layer of refractory metal 21 is deposited above the gate electrode 14 and the source/drain regions 22. Thereafter, one or more anneal processes are performed to convert portions of the layer of refractory metal 21 in contact with the silicon-containing gate electrode 14 and source/drain regions 22 into the metal silicide regions 17, as indicated in FIG. 2B. Then, a wet chemical process is performed to remove unreacted portions of the layer of refractory metal 21, as shown in FIG. 2C.

Referring back to FIG. 1, using current-day technology, the channel length 13 of modern transistors may be approximately 120–180 nm, and further reductions are planned in the future. The reduction in the channel length 13 of the transistor 10 also requires a reduction in the physical size of other components of the transistor 10. For example, the depth of the source/drain regions 22 is also reduced along with the length 12 of the gate electrode 14. As a result of the dramatic reduction of device dimensions, other aspects of the transistor 10 may act to limit the performance characteristics of the transistor. Stated another way, the performance of the transistor 10 may not be limited solely by the channel length 13 of the transistor 10, but rather by the RC-time delay associated with the propagation of electrical signals in an integrated circuit device and within the transistor 10. For example, delays associated with the propagation of an electrical signal along the width, i.e., into the drawing page, of the gate electrode 14 (to turn the transistor "ON") may act to limit one or more operating characteristics of the transistor 10. Similarly, signal propagation may be limited through the source/drain regions 22 of the transistor 10. However, the thickness of metal silicide regions 17 on the source/drain regions 22 must be limited so as not to consume too much of the underlying source/drain regions 22 during the formation process.

In some cases, the process parameters used in forming metal silicide regions 17, e.g., anneal temperatures and duration, the duration of wet chemical processes, etc., may be determined by performing various tests on a number of test wafers. In other cases, e.g., removal of unreacted refractory metal 21, a wet chemical process is performed for a duration that is assumed to be sufficient for the maximum anticipated thickness of the originally formed layer of refractory metal 21. However, the duration of the wet chemical process determined using this "worst case" type approach may unduly consume other components of the transistor 10 if the layer of refractory metal 21 is thinner than the anticipated "worst-case" thickness. For example, depending upon the composition of the material used for the side-wall spacers 20, if the wet chemical process is performed for too long of a duration, it may consume too much of the sidewall spacers 20. As another example, excessive etch time may consume some of the metal silicide regions 17.

Additionally, the anneal processes performed to form the metal silicide regions 17 is typically a timed process that is performed for the specified duration set by the particular process flow. Similarly, the wet chemical process performed to remove the unreacted refractory metal is also a timed process. Such fixed, inflexible processing methodologies may inhibit the formation of metal silicide regions 17 exhibiting the desired characteristics. In some cases, such fixed, inflexible processing techniques may result in the production of integrated circuit products that do not exhibit the desired performance characteristics.

The present invention is directed to various methods and systems that may solve, or at least reduce, some or all of the aforementioned problems.

SUMMARY OF THE INVENTION

The present invention is generally directed to various methods of controlling the formation of metal silicide regions, and a system for performing same. In one illustrative embodiment, the method comprises forming a layer of refractory metal above a feature, performing at least one anneal process to convert a portion of the layer of refractory metal to at least one metal silicide region on the feature, and measuring at least one characteristic of at least one metal silicide region while the anneal process is being performed. In some cases, this characteristic may be a thickness or surface profile of the metal silicide region.

In another illustrative embodiment, the method comprises forming a layer of refractory metal above a feature, performing at least one anneal process to convert a portion of the layer of refractory metal to at least one metal silicide region on the feature, and performing at least one scatterometric measurement of the metal silicide region after at least a portion of the anneal process is performed to determine at least one characteristic of the metal silicide region.

In yet another illustrative embodiment, the method comprises forming a layer of refractory metal above a feature, performing at least one anneal process to convert a portion of the layer of refractory metal to at least one metal silicide region on the feature, performing at least one scatterometric measurement of the metal silicide region after at least a portion of the anneal process is performed to determine at least one characteristic of at least one metal silicide region, and controlling at least one parameter of the anneal process based upon the determined characteristic of the metal silicide region.

In still another illustrative embodiment, the method comprises forming a layer of refractory metal above a feature, performing at least one anneal process to convert a portion of the layer of refractory metal to at least one metal silicide region on the feature, performing at least one scatterometric measurement of the metal silicide region after at least a portion of the anneal process is performed to determine at least one characteristic of the metal silicide region, generating a scatterometric trace for the metal silicide region, and comparing the generated scatterometric trace to a target scatterometric trace.

BRIEF DESCRIPTION OF THE DRAWINGS

The invention may be understood by reference to the following description taken in conjunction with the accompanying drawings, in which like reference numerals identify like elements, and in which.

Figure 1:
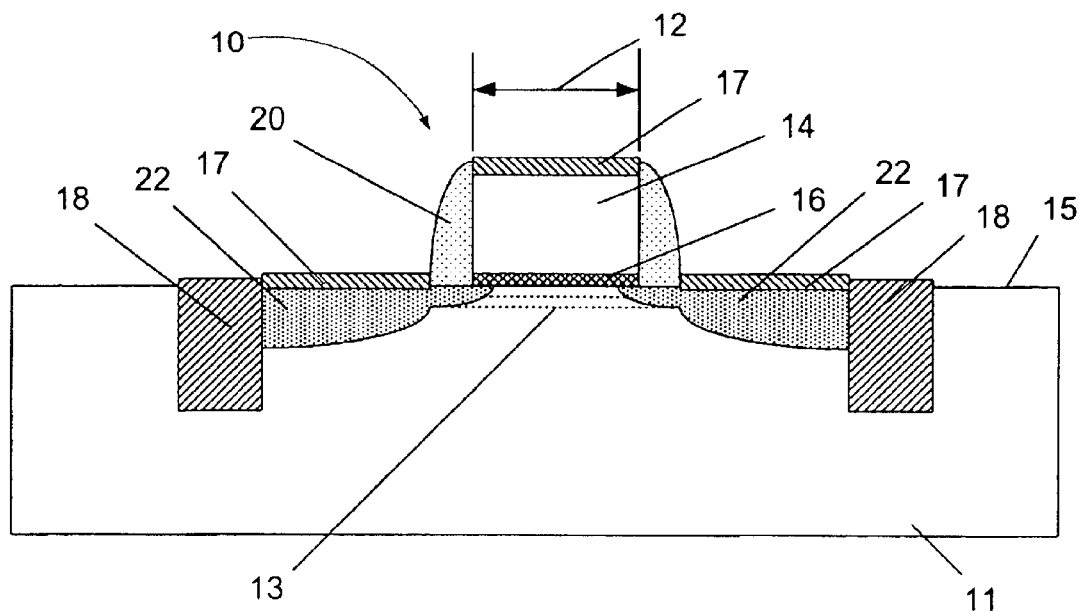
FIG. 1 is a cross-sectional view of an illustrative prior art transistor.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various structures of the semiconductor device and the silicide regions are depicted in the drawings as having very precise, sharp configurations and profiles, those skilled in the art recognize that, in reality, these regions and structures may not be as precise as indicated in the drawings. Additionally, the relative sizes of the various features and silicide regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to various methods of controlling the formation of metal silicide regions on a semiconductor device, and a system for accomplishing same. As will be readily apparent to those skilled in the art upon a complete reading of the present application, the present invention may be employed in connection with the formation of metal silicide regions comprised of a variety of different metal silicides, e.g., cobalt silicide, titanium silicide, tantalum silicide, nickel silicide, platinum silicide, tungsten silicide, etc. Moreover, the present invention may be employed in the context of forming metal silicide regions on any of a variety of different types of semiconductor devices, e.g., transistors, resistors, capacitors, memory cells, light emitting diodes, etc., and it may be employed in connection with the formation of a variety of different types of integrated circuit products, including, but not limited to, logic products, memory products, etc. For convenience, the present invention will be disclosed in the context of the formation of metal silicide regions above an illustrative transistor. However, the present invention should not be considered as limited to the formation of any particular type of metal silicide or to the formation of the metal silicide regions on any particular type of semiconductor device or product unless such limitations are clearly set forth in the appended claims.

The present invention is generally related to a previously filed application, Ser. No. 09/863,596, entitled "Method and Apparatus for Determining Process Layer Thickness Using Scatterometry Measurements," filed May 23, 2001. That application is currently assigned to the assignee of the present invention, Advanced Micro Devices, Inc. The present invention is also related to application Serial No. 1, entitled "Methods of Controlling Wet Chemical Processes in Forming Metal Silicide Regions, and System for Performing Same," filed concurrently with the present application, both of which are hereby incorporated by reference in their entirety.

In general, the formation of metal silicide regions involves depositing a layer of refractory metal on a silicon-containing structure or feature, performing one or more anneal processes to convert at least a portion of the layer of refractory metal into a metal silicide in regions where the refractory metal layer is in contact with the silicon-containing feature, and performing a wet chemical process to remove unreacted portions of the layer of refractory metal. In some cases, a two-step anneal process may be performed to form the metal silicide regions. Moreover, in some other situations, a first anneal process may be performed to initially form a less stable form of metal silicide, followed by a wet chemical process to remove the unreacted refractory metal. Then, a second anneal process may be performed to form a more stable type of metal silicide. The present invention may also be employed in cases where different types of metal silicides that may have differing thicknesses are formed above a semiconductor device. For example, a relatively thick layer of titanium silicide may be formed above the gate electrode 14 while a relatively thin layer of cobalt silicide may be formed above the source/drain regions 22. However, as will be recognized by those skilled in the art after a complete reading of the present application, the present invention is not limited to any particular process flow used to form such metal silicide regions or to any specific material for the metal silicide regions. Thus, such details should not be considered a limitation of the present invention unless such limitations are clearly set forth in the appended claims.

The layer of refractory metal 21 (see FIGS. 3D–3E) may be formed by, for example, a physical vapor deposition (PVD) process or a chemical vapor deposition (CVD) process, and it may be comprised of a variety of materials, e.g., cobalt, nickel, titanium, tantalum, platinum, tungsten, etc. Moreover, the thickness of the layer of refractory metal 21 may vary depending upon the particular application. For example, the layer of refractory metal may vary from approximately 50–300 nm. Thus, the particular type of refractory metal employed, and the manner in which it is made should not be considered a limitation of the present invention. At some point during the process flow, unreacted portions of the layer of refractory metal 21 may be removed by performing a wet chemical process in, for example, a dilute bath. Such a bath may be comprised of, for example, ammonium hydroxide ($NH_4OH$), ammonium hydroxide and hydrogen peroxide ($H_2O_2$), or sulfuric acid and hydrogen peroxide.

In one embodiment, a grating structure is formed that is comprised of a plurality of features upon which metal silicide regions will be formed. The particular feature may vary depending upon the application. For example, the features may be a plurality of line-type features, such as gate electrode structures, or a plurality of doped regions in a substrate, such as source/drain regions. The features may be part of actual production devices or they may be separate test structures formed on a substrate. The physical size of the grating structures, as well as the number of features that comprise each grating structure, may vary depending upon the application.

Figure 3A:
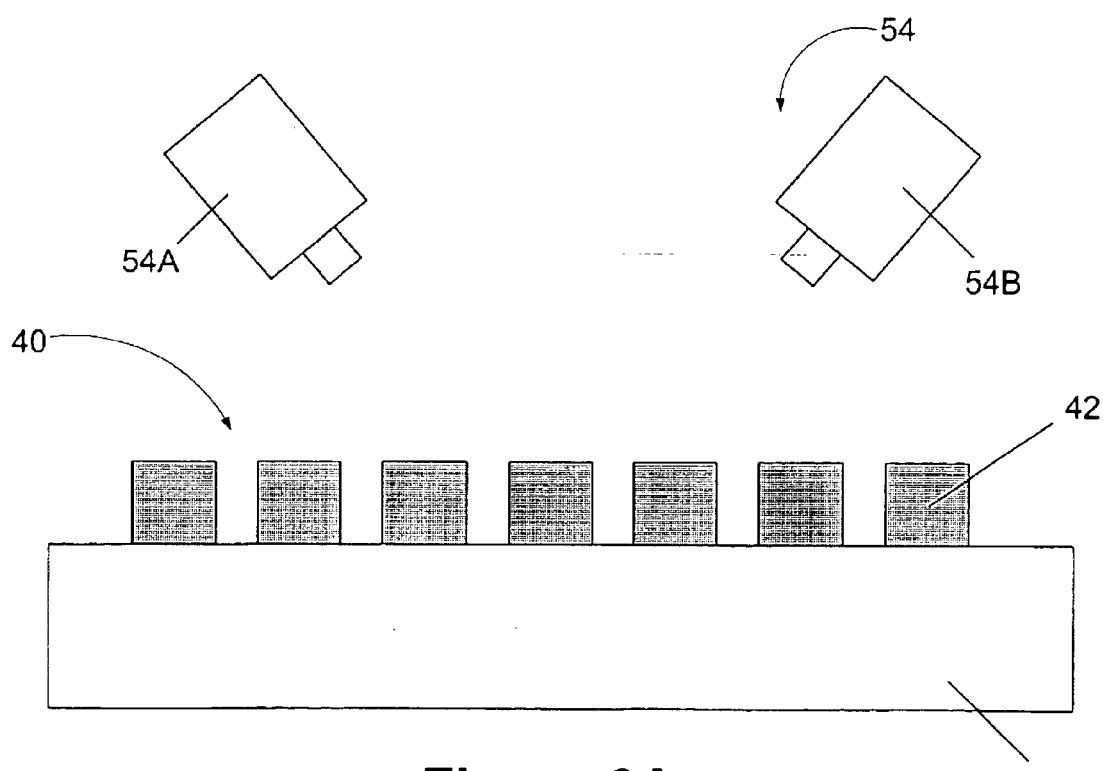
FIG. 3A depicts an illustrative grating structure comprised of a plurality of features.
Figure 2A:
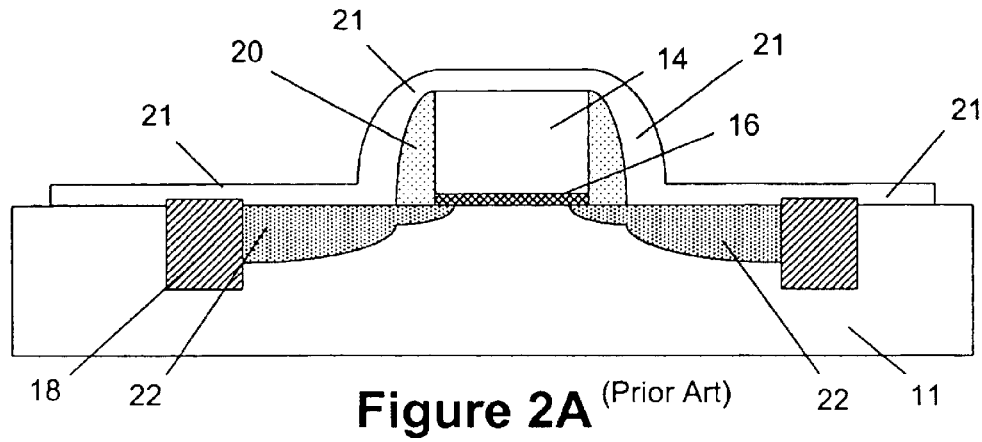
FIGS. 2A–2C are cross-sectional views of an illustrative transistor wherein metal silicide regions are formed above the transistor in accordance with one illustrative prior art process flow.
Figure 2B:
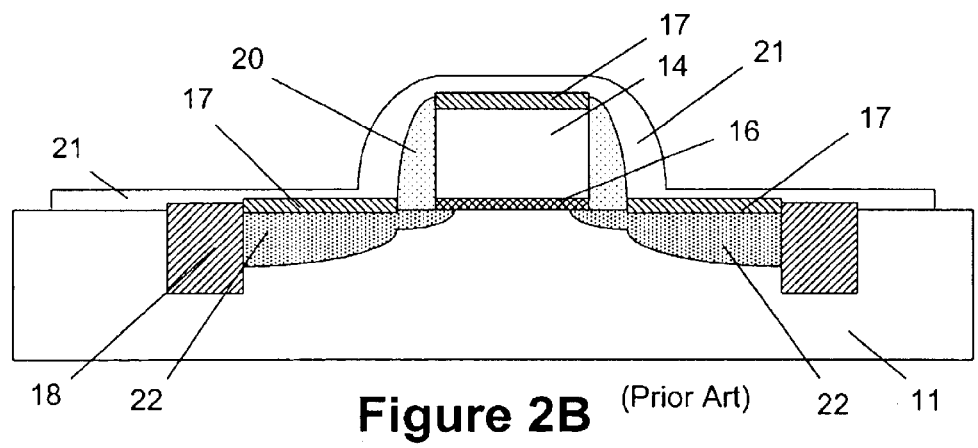
Figure 2C:
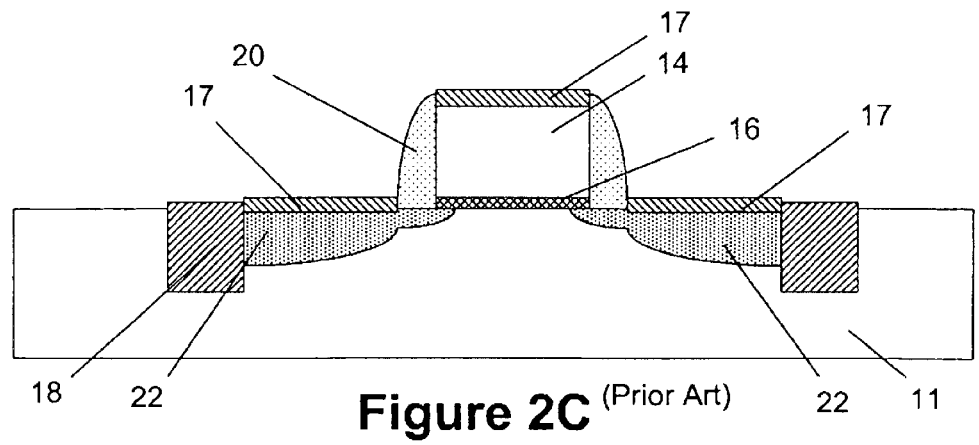

An illustrative grating structure 40 is schematically depicted in FIG. 3A. As described more fully herein, metal silicide regions formed on one or more of the features 42 of the grating structure 40 may be measured using an optical metrology tool, such as a scatterometry tool 54, that is comprised of an illustrative light source 54A and a detector 54B. As stated previously, the features 42 may be any type of structure, e.g., gate electrodes, doped regions, memory cells, etc. For ease of discussion, the features 42 are simply depicted as line-type features.

Figure 3B:
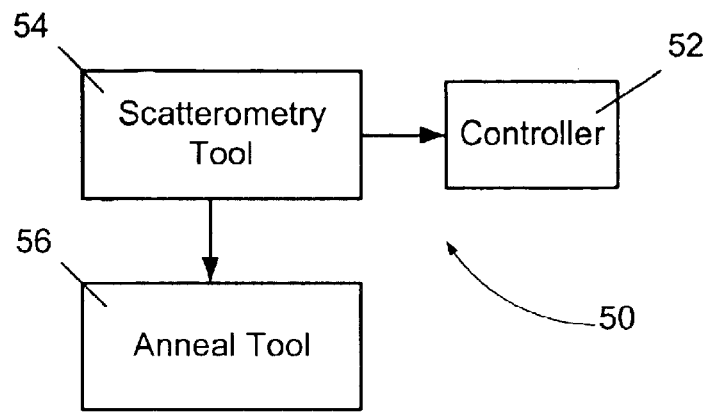
FIG. 3B depicts a system in accordance with one illustrative embodiment of the present invention.
Figure 3C:
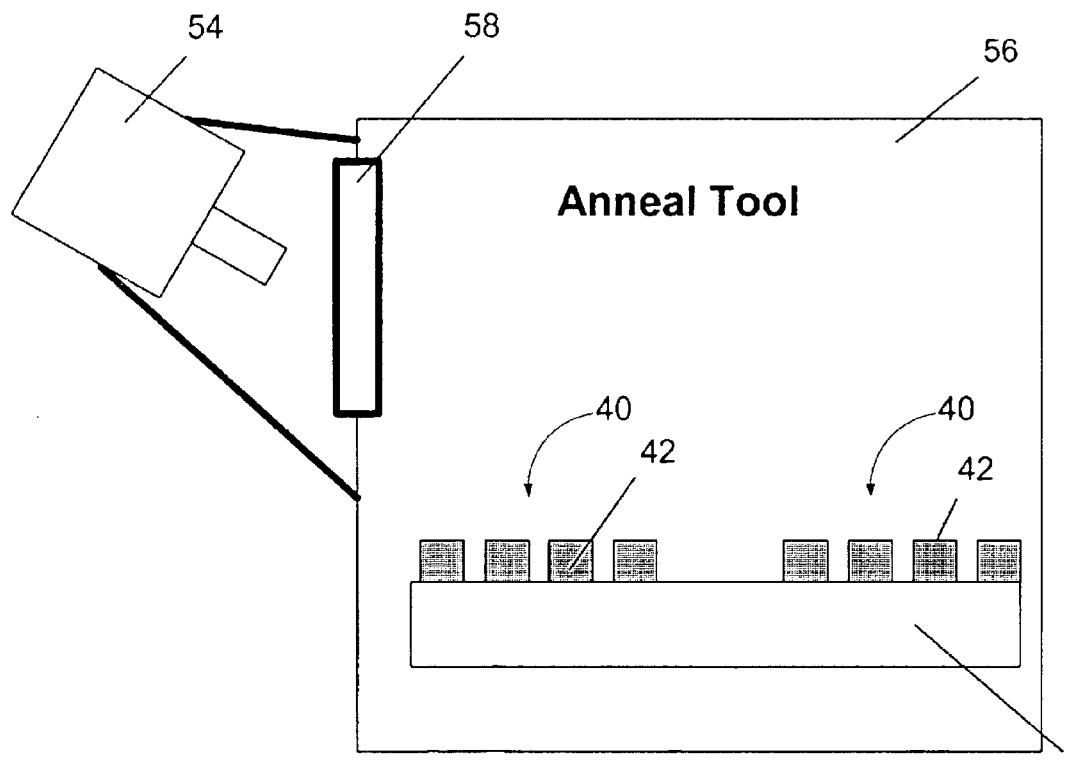
FIG. 3C depicts an illustrative anneal tool in accordance with one illustrative embodiment of the present invention.

FIG. 3B depicts an illustrative system 50 that may be used in accordance with one embodiment of the present invention. As shown therein, the system 50 is comprised of a controller 52, a scatterometry tool 54 and an anneal tool 56. In accordance with one aspect of the present invention, the scatterometry tool 54 is used to monitor the formation of the metal silicide regions 17 in the anneal tool 56. In one particularly illustrative embodiment, the scatterometry tool 54 is used to monitor the formation of the metal silicide regions 17 on an illustrative wafer 11 in the anneal tool 56 through a window 58. That is, the scatterometry tool 54 may be used to take in situ measurements of the metal silicide regions 17 as they are being formed in the anneal tool 56. In the illustrative example depicted in FIG. 3C, the wafer 1 is depicted as having two representative grating structures 40 formed above the wafer 11. However, as will be understood by those skilled in the art after a complete reading of the present application, the number of grating structures 40 formed above the wafer 11, as well as the number and type of features 42 that make up such grating structures, may vary.

Figure 3D:
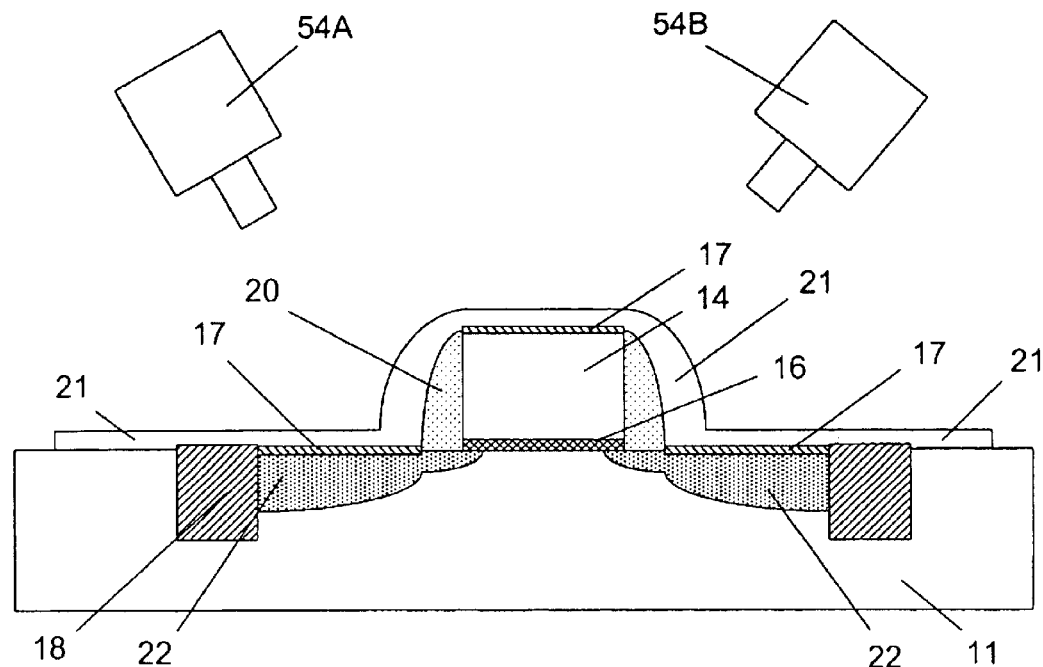
FIGS. 3D–3E depict an illustrative transistor having metal silicide regions formed thereabove wherein the formation of the metal silicide regions is controlled in accordance with one embodiment of the present invention.
Figure 3E:
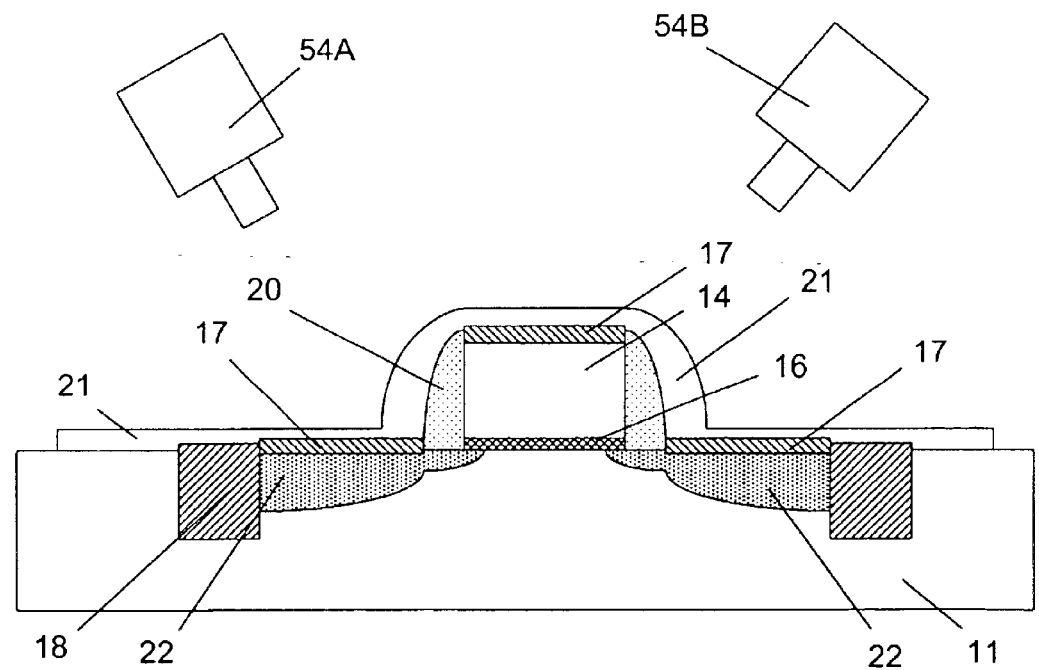

FIGS. 3D and 3E are enlarged cross-sectional views of an illustrative wafer 11 depicting an illustrative example of how the present invention may be employed. In this example, the grating structures 40 are comprised of a plurality of transistors 10 wherein metal silicide regions 17 will be formed on the gate electrode 14 and the source/drain regions 22. FIG. 3D depicts the situation where the formation of the metal silicide regions 17 is just beginning, whereas FIG. 3E depicts the situation where the formation of the metal silicide regions 17 is complete. In both cases, the scatterometry tool 54, comprised of an illustrative light source 54A and detector 54B, is used to illuminate the metal silicide regions 17 at some point during the formation of the metal silicide regions 17 and collect light reflected from the metal silicide regions 17. In one very specific embodiment, the scatterometry tool 54 is used to measure one or more characteristics of the metal silicide regions 17 as the anneal process is being performed in the anneal tool 56. As the metal silicide regions 17 are being formed, the optical characteristics of the metal silicide regions 17 may change. Based upon these scatterometric measurements, various characteristics of the metal silicide regions 17 may be determined, such as thickness, chemical stoichiometry, and surface profile, e.g., irregularities such as voids or agglomerations.

The metrology data from the scatterometry tool 54 may be provided to the controller 52. Based upon an analysis of the data obtained by the scatterometry tool 54, the controller may control one or more parameters of the anneal process performed in the anneal tool 56. For example, the controller 52 may act to increase or decrease the temperature of the anneal process and/or stop (endpoint) the anneal process. The controller 52 may also act to control parameters such as temperature ramp rate, gas flow rates, gas composition, pressure, etc. In one particularly illustrative embodiment, the controller 52 may be used to stop the anneal process when the data from the scatterometry tool 54 indicates that the metal silicide regions 17 have reached a desired, target thickness.

In another illustrative embodiment, the data obtained by the scatterometry tool 54 may be used to control or adjust at least one parameter of an anneal process to be performed in forming metal silicide regions 17 on a subsequently processed substrate. That is, in this embodiment, the scatterometric data may be used to regulate the anneal process performed on subsequently processed substrates in the anneal tool 56.

In performing the actions described above, the scatterometry tool 54 may be used to measure any or all of the metal silicide regions 17 formed above one or more semiconductor devices, e.g., transistors, formed above one or more wafers 11. For example, the scatterometry tool 54 may be used to measure the thickness of the metal silicide regions 17 formed above the source/drain regions 22, and various control actions may be taken on the basis of such measurements. Given the very small depth of source/drain regions 22 on modern transistor devices, it is very important to control the thickness of the metal silicide regions 17 formed above the source/drain regions 17. Of course, if desired, the scatterometry tool 54 could be focused on the metal silicide regions 17 formed above the gate electrode 14, and control actions could be taken based upon the resulting measurement data.

A variety of scatterometry type tools may be used with the present invention, e.g., so-called 2θ-type systems and lens-type scatterometry tools. The scatterometry tool 54 may use white light, or some other wavelength or combination of wavelengths, depending on the specific implementation. Typically, the light source 54A will generate an incident beam that has a wide spectral composition and wherein the intensity of the reflected light changes slowly in comparison to changes in wavelength. The angle of incidence of the light may also vary, depending on the specific implementation. For example, a spectroscopic ellipsometer (single angle, many wavelengths), or a laser (single wavelength, many angles) may be used with the present invention. Additionally, the light source 54A and the detector 54B may be arranged in a concentric circle configuration, with the light source 54A illuminating the metal silicide regions from a perpendicular orientation, e.g., a reflectometer. The intensity of the reflected light may be measured as s- and p-polarization over either multiple angles or at multiple wavelengths.

In general, the scatterometry tool 54 includes optical hardware, such as an ellipsometer or reflectometer, and a data processing unit loaded with a scatterometry software application for processing data collected by the optical hardware. For example, the optical hardware may include a Model OP5230 or OP5240 with a spectroscopic ellipsometer offered by Thermawave, Inc. of Fremont, Calif. The data processing unit may comprise a profile application server manufactured by Timbre Technologies, a fully owned subsidiary of Tokyo Electron America, Inc. of Austin, Tex. and distributed by Thermawave, Inc.

The anneal tool 56 may be any type of tool useful for performing the anneal process or processes to form the metal silicide regions 17. For example, the anneal tool 56 may be a furnace or a rapid thermal anneal (RTA) chamber. The particular anneal process parameters, e.g., temperature, duration, temperature ramp rate, gas flow rates, gas composition, pressure, etc., may vary depending upon the application. In one illustrative embodiment, where the refractory metal layer 21 is comprised of titanium, the anneal tool 56 may be an RTA chamber that is used to perform a first anneal process at a temperature ranging from approximately 450–550° C. and then to perform a second anneal process at a temperature of approximately 700–850° C.

In the illustrated embodiment, the controller 52 is a computer programmed with software to implement the functions described herein. Moreover, the functions described for the controller 52 may be performed by one or more controllers spread through the system. For example, the controller 52 may be a fab level controller that is used to control processing operations throughout all or a portion of a semiconductor manufacturing facility. Alternatively, the controller 52 may be a lower level computer that controls only portions or cells of the manufacturing facility. Moreover, the controller 52 may be a stand-alone device, or it may reside on the scatterometry tool 54 or the anneal tool 56. However, as will be appreciated by those of ordinary skill in the art, a hardware controller (not shown) designed to implement the particular functions may also be used.

Variations in one or more of the characteristics of the metal silicide regions 17, e.g., thickness, surface profile, chemical stoichiometry, etc., will cause a change in the diffraction characteristics of the incident light from the light source 54A. In one embodiment, the present invention involves taking scatterometric measurements of the metal silicide regions 17 at some point during their manufacture, and comparing a scatterometric trace generated during the scatterometric measurement to a target trace that corresponds to a metal silicide region 17 having a desired or target characteristic. For example, based upon Maxwell's equations, a target trace may be created that corresponds to a metal silicide region 17 having a desired or target thickness. In this embodiment, the controller 52 may monitor data obtained by the scatterometry tool 54 to control one or more parameters of the anneal process preformed in the anneal tool 56. For example, based upon a comparison of the trace generated by the scatterometry tool 54 and the target trace, the controller 52 may adjust or modify the temperature and/or duration of the anneal process. The controller 52 may also control parameters such as temperate ramp rate, gas flow rates, gas composition, etc. In one particularly illustrative example, the controller 52 may stop the anneal process when the generated scatterometry trace closely matches the target trace. In this manner, the anneal process may be controlled so as to result in metal silicide regions 17 that exhibit the target characteristic, e.g., thickness, associated with the target trace. The comparison between such traces may be made using a variety of techniques known to those skilled in the relevant art. In one very specific embodiment, the scatterometric measurements of the metal silicide regions may be performed at the same time that the anneal process is being performed to form the metal silicide regions.

In another embodiment, using scatterometric techniques, a unique profile trace may be established for each unique characteristic of the metal silicide regions 17, e.g., thickness, width, surface irregularities, chemical stoichiometry, etc., that may be expected. A library of profile traces corresponding to each unique characteristic of the metal silicide regions 17 may be created and stored in a library. Thereafter, using known matching techniques, a scatterometric trace may be generated by the scatterometry tool 54 and this generated scatterometric trace may be matched to the closest corresponding trace in the library. Based upon this match, the measured metal silicide region 17 is determined to have a characteristic, e.g., thickness, surface irregularities, etc., that corresponds to the characteristic associated with the matched trace from the library. Scatterometry libraries are commercially available from Timbre Technologies, Inc. Although not necessary, if desired, the library of calculated profile traces may be confirmed by various destructive metrology tests, where a scatterometry profile trace is generated and the actual characteristic, e.g., thickness, of the metal silicide region 17 is subsequently measured using a scanning electron microscope metrology technique. Obviously, the number of combinations used to create the library may vary as a matter of design choice. Moreover, the greater the number of combinations, the greater will be the library containing the appropriate signature profiles of the implant regions. In some embodiments of the invention, by allowing "n" and "k" to vary with depth and/or chemical stoichiometry, the library of signature traces may be relatively large due to the additional variables in the values for "n" and "k." However, given the importance of accurately forming various metal silicide regions 17, the additional computing power and storage required may be warranted.

The scatterometry tool 54 is used to generate a scatterometric trace for a given metal silicide region. The scatterometry tool 54 may sample one or more metal silicide regions on a given wafer in a lot or even generate a scatterometric trace for a plurality of metal silicide regions in the lot, depending on the specific implementation. Moreover, the scatterometric traces from a sample of the metal silicide regions may be averaged or otherwise statistically analyzed.

Figure 4:
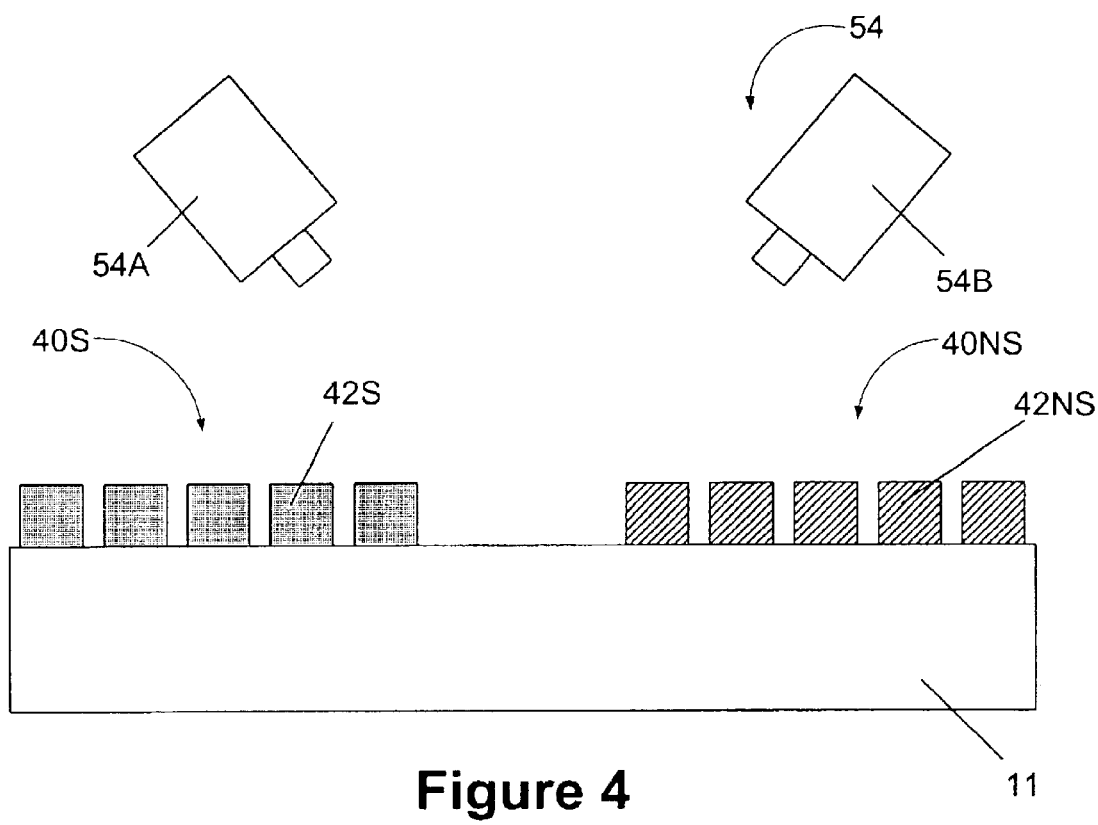
FIG. 4 depicts a wafer having a plurality of grating structures formed thereabove in accordance with another aspect of the present invention.

FIG. 4 represents another aspect of the present invention. As shown therein, at least two grating structures 40S and 40NS are formed above the wafer 11. The grating structure 40S is comprised of features 42S upon which metal silicide regions may be formed, whereas the grating structure 40NS is comprised of features 42NS where metal silicide regions will not readily form. For example, the features 42S may be comprised of silicon-containing materials, such as polysilicon or doped silicon regions, whereas the features 42NS may be comprised of, e.g., silicon dioxide, silicon nitride, or some other material where metal silicide regions will not readily form. Using this approach, the grating structure 40NS may serve as a reference point for determining a characteristic, e.g., thickness, of metal silicide regions formed on the features 42S of the grating structure 40S. This approach may also be used to determine the thickness of the unreacted refractory metal that is to be subsequently stripped and/or to determine the total thickness of the incoming layer of refractory metal that is to be reacted to form the metal silicide regions.

For ease of reference, the features 42S, 42NS are depicted as line-type features. However, as discussed previously with respect to the features 42 of the grating structure 40, the features 42S, 42NS may be of any type and configuration, and the number of features 42S, 42NS that comprise the depicted grating structures may vary. Moreover, although two grating structures 42S, 42NS are depicted in the drawing, any number of such grating structures may be formed above the wafer 11. For example, several of the grating structures 42S, where silicide regions may be formed, may be created on the wafer 11, while only one of the grating structures 42NS may be formed to serve as a reference for all of the other grating structures 42S.

In this embodiment, the scatterometry tool 54 may be used to take scatterometric measurements of metal silicide regions formed on the features 42S of the grating structure 40S. The scatterometry tool 54 may also be used to obtain scatterometric measurements of the features 42NS of the grating structure 40NS. Based upon a comparison of the two generated scatterometric traces, a characteristic, e.g., thickness of the metal silicide regions formed on the features 42S, may be determined. If desired, various control actions may be taken based upon the determined characteristic, e.g., the anneal process may be stopped, the temperature may be varied, or other process parameters, such as temperature ramp rate, gas composition, gas flow rates, etc., may also be varied. The combination of data obtained from measurement of both the grating structures 40S and 40NS may also be used to control one or more aspects of the anneal process.

Modernm integrated circuit manufacturing involves the formation of extremely thin metal silicide layers, and further reductions in thickness are anticipated in the future. Thus, by providing this standard grating structure 40NS where metal silicide regions will not form, more accurate measurements may be made as to the characteristics, e.g., thickness of the metal silicide regions, that are actually formed.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 52, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699-Provisional Specification for CIM Framework Domain Architecture) and APC (SEMI E93-0999-Provisional Specification for CIM Framework Advanced Process Control Component) specifications are publicly available from SEMI.

The present invention is generally directed to various methods of controlling the formation of metal silicide regions, and a system for performing same. In one illustrative embodiment, the method comprises forming a layer of refractory metal above a feature, performing at least one anneal process to convert a portion of the layer of refractory metal to at least one metal silicide region on the feature, and measuring at least one characteristic of the metal silicide region while the anneal process is being performed. The measured characteristic may include, for example, a thickness or surface profile of the metal silicide region.

In another illustrative embodiment, the method comprises forming a layer of refractory metal above a feature, performing at least one anneal process to convert a portion of the layer of refractory metal to at least one metal silicide region on the feature, and performing at least one scatterometric measurement of the metal silicide region after at least a portion of the anneal process is performed to determine at least one characteristic of the metal silicide region. In further embodiments, the method further comprises controlling at least one parameter of the anneal process based upon the determined characteristic of the metal silicide region.

In yet another illustrative embodiment, the method comprises forming a layer of refractory metal above a feature, performing at least one anneal process to convert a portion of the layer of refractory metal to at least one metal silicide region on the feature, performing at least one scatterometric measurement of the metal silicide region after at least a portion of the anneal process is performed to determine at least one characteristic of the metal silicide region, generating a scatterometric trace for the metal silicide region, and comparing the generated scatterometric trace to a target scatterometric trace.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of forming metal silicide regions, comprising:

forming a layer of refractory metal above a feature;

performing at least one anneal process to convert a portion of said layer of refractory metal to at least one metal silicide region on said feature; and measuring at least one characteristic of said at least one metal silicide region using a scatterometry tool while said at least one anneal process is being performed.

2. The method of claim 1, wherein said feature is comprised of at least one of a gate electrode, a source region, a drain region, a silicon-containing line, a resistor, a capacitor, a memory cell and a transistor.

3. The method of claim 1, wherein said refractory metal is comprised of at least one of cobalt, titanium, tantalum, nickel, platinum and tungsten.

4. The method of claim 1, wherein said at least one metal silicide region is comprised of at least one of cobalt silicide, titanium silicide, tantalum silicide, nickel silicide, platinum silicide and tungsten silicide.

5. The method of claim 1, wherein said at least one anneal process is performed in at least one of a furnace and a rapid thermal anneal chamber.

6. The method of claim 1, wherein performing at least one anneal process comprises performing two anneal processes, a first of said anneal processes being performed at a temperature that is less than a temperature of a second of said anneal processes.

7. The method of claim 1, wherein said at least one characteristic of said at least one metal silicide region is comprised of at least one of a thickness, a surface profile and a chemical stoichiometry of said at least one metal silicide region.

8. The method of claim 1, further comprising performing at least one wet chemical process to remove unreacted portions of said layer of refractory metal.

9. The method of claim 1, further comprising controlling at least one parameter of said at least one anneal process based upon said determined at least one characteristic of said at least one metal silicide region.

10. The method of claim 9, wherein said at least one parameter is comprised of at least one of a temperature, a duration, a gas composition, a gas flow rate, and a temperature ramp rate of said at least one anneal process.

11. The method of claim 1, wherein measuring at least one characteristic of said at least one metal silicide region comprises illuminating at least one metal silicide region and measuring light reflected therefrom.

12. The method of claim 1, wherein measuring at least one characteristic of said at least one metal silicide region comprises:

generating a scatterometric trace for said at least one metal silicide region; and comparing said generated scatterometric trace to a target scatterometric trace.

13. The method of claim 1, wherein measuring at least one characteristic of said at least one metal silicide region comprises:

generating a scatterometric trace for said at least one metal silicide region;

creating a target scatterometric trace for said at least one metal silicide region; and comparing said generated scatterometric trace to said target scatterometric trace.

14. The method of claim 1, further comprising modifying, based upon said measured characteristic of said at least one metal silicide region, at least one parameter of at least one anneal process to be performed to form at least one metal silicide region on at least one subsequently processed substrate.

15. A method of forming metal silicide regions, comprising:

forming a layer of refractory metal above a feature;

performing at least one anneal process to convert a portion of said layer of refractory metal to at least one metal silicide region on said feature; and performing at least one scatterometric measurement of said at least one metal silicide region after at least a portion of said at least one anneal process is performed to determine at least one characteristic of said at least one metal silicide region.

16. The method of claim 15, wherein said feature is comprised of at least one of a gate electrode, a source region, a drain region, a silicon-containing line, a resistor, a capacitor, a memory cell and a transistor.

17. The method of claim 15, wherein said refractory metal is comprised of at least one of cobalt, titanium, tantalum, nickel, platinum and tungsten.

18. The method of claim 15, wherein said at least one metal silicide region is comprised of at least one of cobalt silicide, titanium silicide, tantalum silicide, nickel silicide, platinum silicide and tungsten silicide.

19. The method of claim 15, wherein said at least one anneal process is performed in at least one of a furnace and a rapid thermal anneal chamber.

20. The method of claim 15, wherein performing at least one anneal process comprises performing two anneal processes, a first of said anneal processes being performed at a temperature that is less than a temperature of a second of said anneal processes.

21. The method of claim 15, wherein said at least one characteristic of said at least one metal silicide region is comprised of at least one of a thickness, a surface profile and a chemical stoichiometry of said at least one metal silicide region.

22. The method of claim 15, further comprising performing at least one wet chemical process to remove unreacted portions of said layer of refractory metal.

23. The method of claim 15, further comprising controlling at least one parameter of said at least one anneal process based upon said determined at least one characteristic of said at least one metal silicide region.

24. The method of claim 23, wherein said at least one parameter is comprised of at least one of a temperature, a duration, a gas composition, a gas flow rate, and a temperature ramp rate of said at least one anneal process.

25. The method of claim 15, wherein performing said at least one scatterometric measurement of said at least one metal silicide region comprises illuminating at least one metal silicide region and measuring light reflected therefrom.

26. The method of claim 15, wherein performing said at least one scatterometric measurement of said at least one metal silicide region comprises:

generating a scatterometric trace for said at least one metal silicide region; and comparing said generated scatterometric trace to a target scatterometric trace.

27. The method of claim 15, wherein performing said at least one scatterometric measurement of said at least one metal silicide region comprises:

generating a scatterometric trace for said at least one metal silicide region;

creating a target scatterometric trace for said at least one metal silicide region; and comparing said generated scatterometric trace to said target scatterometric trace.

28. The method of claim 15, further comprising modifying, based upon said determined characteristic of said at least one metal silicide region, at least one parameter of at least one anneal process to be performed to form at least one metal silicide region on at least one subsequently processed substrate.

29. The method of claim 15, wherein said scatterometric measurement is performed while said at least one anneal process is being performed.

30. A method of forming metal silicide regions, comprising:

forming a layer of refractory metal above a feature;

performing at least one anneal process to convert a portion of said layer of refractory metal to at least one metal silicide region on said feature;

performing at least one scatterometric measurement of said at least one metal silicide region after at least a portion of said at least one anneal process is performed to determine at least one characteristic of said at least one metal silicide region; and controlling at least one parameter of said at least one anneal process based upon said determined at least one characteristic of said at least one metal silicide region.

31. The method of claim 30, wherein said feature is comprised of at least one of a gate electrode, a source region, a drain region, a silicon-containing line, a resistor, a capacitor, a memory cell and a transistor.

32. The method of claim 30, wherein said refractory metal is comprised of at least one of cobalt, titanium, tantalum, nickel, platinum and tungsten.

33. The method of claim 30, wherein said at least one metal silicide region is comprised of at least one of cobalt silicide, titanium silicide, tantalum silicide, nickel silicide, platinum silicide and tungsten silicide.

34. The method of claim 30, wherein said at least one anneal process is performed in at least one of a furnace and a rapid thermal anneal chamber.

35. The method of claim 30, wherein performing at least one anneal process comprises performing two anneal processes, a first of said anneal processes being performed at a temperature that is less than a temperature of a second of said anneal processes.

36. The method of claim 30, wherein said at least one characteristic of said at least one metal silicide region is comprised of at least one of a thickness, a surface profile and a chemical stoichiometry of said at least one metal silicide region.

37. The method of claim 30, further comprising performing at least one wet chemical process to remove unreacted portions of said layer of refractory metal.

38. The method of claim 30, wherein said at least one parameter of said at least one anneal process is comprised of at least one of a temperature, a duration, a gas composition, a gas flow rate, and a temperature ramp rate of said at least one anneal process.

39. The method of claim 30, wherein performing said at least one scatterometric measurement of said at least one metal silicide region comprises illuminating at least one metal silicide region and measuring light reflected therefrom.

40. The method of claim 30, wherein performing said at least one scatterometric measurement of said at least one metal silicide region comprises:
generating a scatterometric trace for said at least one metal silicide region;
creating a scatterometric trace for a metal silicide region having at least one specific characteristic; and
comparing said generated scatterometric trace to said created scatterometric trace.

41. The method of claim 30, wherein performing said at least one scatterometric measurement of said at least one metal silicide region comprises:
generating a scatterometric trace for said at least one metal silicide region;
creating a target scatterometric trace for said at least one metal silicide region; and
comparing said generated scatterometric trace to said target scatterometric trace.

42. The method of claim 30, further comprising modifying, based upon said determined characteristic of said at least one metal silicide region, at least one parameter of at least one anneal process to be performed to form at least one metal silicide region on at least one subsequently processed substrate.

43. A method of forming metal silicide regions, comprising:
forming a layer of refractory metal above a feature;
performing at least one anneal process to convert a portion of said layer of refractory metal to at least one metal silicide region on said feature;
performing at least one scatterometric measurement of said at least one metal silicide region after at least a portion of said anneal process is performed to determine a thickness of said at least one metal silicide region; and
controlling at least one of a duration and a temperature of said at least one anneal process based upon said determined thickness of said at least one metal silicide region.

44. The method of claim 43, wherein said feature is comprised of at least one of a gate electrode, a source region, a drain region, a silicon-containing line, a resistor, a capacitor, a memory cell and a transistor.

45. The method of claim 43, wherein said refractory metal is comprised of at least one of cobalt, titanium, tantalum, nickel, platinum and tungsten.

46. The method of claim 43, wherein said at least one metal silicide region is comprised of at least one of cobalt silicide, titanium silicide, tantalum silicide, nickel silicide, platinum silicide and tungsten silicide.

47. The method of claim 43, wherein said at least one anneal process is performed in at least one of a furnace and a rapid thermal anneal chamber.

48. The method of claim 43, further comprising performing at least one wet chemical process to remove unreacted portions of said layer of refractory metal.

49. The method of claim 43, wherein performing said at least one scatterometric measurement of said at least one metal silicide region comprises:
generating a scatterometric trace for said at least one metal silicide region;
creating a scatterometric trace for a metal silicide region having a specific thickness characteristic; and
comparing said generated scatterometric trace to said created scatterometric trace.

50. The method of claim 43, wherein performing said at least one scatterometric measurement of said at least one metal silicide region comprises:
generating a scatterometric trace for said at least one metal silicide region;
creating a target scatterometric trace for said at least one metal silicide region; and
comparing said generated scatterometric trace to said target scatterometric trace.

51. The method of claim 43, further comprising modifying, based upon said determined thickness of said at least one metal silicide region, at least one parameter of at least one anneal process to be performed to form at least one metal silicide region on at least one subsequently processed substrate.

52. A method of forming metal silicide regions, comprising:
forming a layer of refractory metal above a feature;
performing at least one anneal process to convert a portion of said layer of refractory metal to at least one metal silicide region on said feature;
generating a scatterometric trace for said at least one metal silicide region after at least a portion of said at least one anneal process is performed;
obtaining a target scatterometric trace that is based upon a target value for at least one characteristic of said at least one metal silicide region; and
comparing said generated scatterometric trace to said target scatterometric trace.

53. The method of claim 52, wherein said feature is comprised of at least one of a gate electrode, a source region, a drain region, a silicon-containing line, a resistor, a capacitor, a memory cell and a transistor.

54. The method of claim 52, wherein said target scatterometric trace is created based upon calculations.

55. The method of claim 52, wherein said refractory metal is comprised of at least one of cobalt, titanium, tantalum, nickel, platinum and tungsten.

56. The method of claim 52, wherein said at least one metal silicide region is comprised of at least one of cobalt silicide, titanium silicide, tantalum silicide, nickel silicide, platinum silicide and tungsten silicide.

57. The method of claim 52, wherein said at least one anneal process is performed in at least one of a furnace and a rapid thermal anneal chamber.

58. The method of claim 52, wherein performing at least one anneal process comprises performing two anneal processes, a first of said anneal processes being performed at a temperature that is less than a temperature of a second of said anneal processes.

59. The method of claim 52, wherein said target scatterometric trace for said at least one metal silicide region is based upon a target value for at least one of a thickness and a surface profile of said at least one metal silicide region.

60. The method of claim 52, wherein said generated scatterometric trace and said target scatterometric trace are compared to determine a characteristic of said at least one metal silicide region formed during said at least one anneal process.

61. The method of claim 52, further comprising performing at least one wet chemical process to remove unreacted portions of said layer of refractory metal.

62. The method of claim 61, wherein said at least one parameter is comprised of at least one of a temperature, a duration, a gas composition, a gas flow rate, and a temperature ramp rate of said at least one anneal process.

63. The method of claim 52, further comprising controlling at least one parameter of said at least one anneal process based upon said comparison of said generated scatterometric trace and said target trace.

64. The method of claim 52, further comprising modifying, based upon said comparison of said generated scatterometric trace and said target trace, at least one parameter of at least one anneal process to be performed to form at least one metal silicide region on at least one subsequently processed substrate.

65. A method, comprising:
forming a plurality of grating structures above a semiconducting substrate, a first of said grating structures being comprised of a plurality of features on which a metal silicide region may be formed, a second of said grating structures being comprised of features on which substantially no metal silicide region will be formed;
forming a metal silicide region on at least one of said features of said first grating structure;
performing at least one scatterometric measurement on at least one feature in each of said first and second grating structures after said at least one metal silicide region has been at least partially formed; and
determining at least one characteristic of said at least one metal silicide region based upon a comparison of said scatterometric measurement of said at least one feature in said first grating structure and said scatterometric measurement of said at least one feature in said second grating structure.

66. The method of claim 65, wherein said features of said first grating structure are comprised of polysilicon.

67. The method of claim 65, wherein said features of said second grating structure are comprised of silicon dioxide or silicon nitride.

68. The method of claim 65, wherein said features in each of said plurality of grating structures are line features.

69. The method of claim 65, wherein said at least one metal silicide region is comprised of at least one of cobalt silicide, titanium silicide, tantalum silicide, nickel silicide, platinum silicide and tungsten silicide.

70. The method of claim 65, wherein forming said metal silicide region comprises performing at least one anneal process.

71. The method of claim 65, wherein said at least one characteristic of said at least one metal silicide region is comprised of at least one of a thickness, a surface profile and a chemical stoichiometry of said at least one metal silicide region.

72. The method of claim 65, further comprising performing at least one wet chemical process to remove unreacted portions of said layer of refractory metal.

73. The method of claim 65, further comprising controlling at least one parameter of at least one anneal process performed to form said metal silicide region based upon said determined at least one characteristic of said at least one metal silicide region.

74. The method of claim 73, wherein said at least one parameter is comprised of at least one of a temperature, a duration, a gas composition, a gas flow rate, and a temperature ramp rate of said at least one anneal process.

75. A method of forming metal silicide regions, comprising:
forming a layer of refractory metal above a feature;
performing at least one anneal process to convert a portion of said layer of refractory metal to at least one metal silicide region on said feature; and
measuring at least one characteristic of said at least one metal silicide region while said at least one anneal process is being performed, wherein measuring said at least one characteristic of said at least one metal silicide region comprises illuminating at least one metal silicide region and measuring light reflected therefrom.

76. The method of claim 75, wherein said feature is comprised of at least one of a gate electrode, a source region, a drain region, a silicon-containing line, a resistor, a capacitor, a memory cell and a transistor.

77. The method of claim 75, wherein said at least one characteristic of said at least one metal silicide region is comprised of at least one of a thickness, a surface profile and a chemical stoichiometry of said at least one metal silicide region.

78. The method of claim 75, further comprising controlling at least one parameter of said at least one anneal process based upon said determined at least one characteristic of said at least one metal silicide region.

79. The method of claim 78, wherein said at least one parameter is comprised of at least one of a temperature, a duration, a gas composition, a gas flow rate, and a temperature ramp rate of said at least one anneal process.

80. The method of claim 75, further comprising modifying, based upon said measured characteristic of said at least one metal silicide region, at least one parameter of at least one anneal process to be performed to form at least one metal silicide region on at least one subsequently processed substrate.

81. A method of forming metal silicide regions, comprising:
forming a layer of refractory metal above a feature;
performing at least one anneal process to convert a portion of said layer of refractory metal to at least one metal silicide region on said feature; and
measuring at least one characteristic of said at least one metal silicide region while said at least one anneal process is being performed, wherein measuring said at least one characteristic of said at least one metal silicide region comprises: generating a scatterometric trace for said at least one metal silicide region; and comparing said generated scatterometric trace to a target scatterometric trace.

82. The method of claim 81, wherein said at least one characteristic of said at least one metal silicide region is comprised of at least one of a thickness, a surface profile and a chemical stoichiometry of said at least one metal silicide region.

83. The method of claim 81, further comprising controlling at least one parameter of said at least one anneal process based upon said determined at least one characteristic of said at least one metal silicide region.

84. The method of claim 83, wherein said at least one parameter is comprised of at least one of a temperature, a duration, a gas composition, a gas flow rate, and a temperature ramp rate of said at least one anneal process.

85. The method of claim 81, further comprising modifying, based upon said measured characteristic of said at least one metal silicide region, at least one parameter of at least one anneal process to be performed to form at least one metal silicide region on at least one subsequently processed substrate.

86. A method of forming metal silicide regions, comprising:

forming a layer of refractory metal above a feature;

performing at least one anneal process to convert a portion of said layer of refractory metal to at least one metal silicide region on said feature; and measuring at least one characteristic of said at least one metal silicide region while said at least one anneal process is being performed, wherein measuring said at least one characteristic of said at least one metal silicide region comprises: generating a scatterometric trace for said at least one metal silicide region; creating a target scatterometric trace for said at least one metal silicide region; and comparing said generated scatterometric trace to said target scatterometric trace.

87. The method of claim 86, wherein said at least one characteristic of said at least one metal silicide region is comprised of at least one of a thickness, a surface profile and a chemical stoichiometry of said at least one metal silicide region.

88. The method of claim 86, further comprising controlling at least one parameter of said at least one anneal process based upon said determined at least one characteristic of said at least one metal silicide region.

89. The method of claim 88, wherein said at least one parameter is comprised of at least one of a temperature, a duration, a gas composition, a gas flow rate, and a temperature ramp rate of said at least one anneal process.

90. The method of claim 86, further comprising modifying, based upon said measured characteristic of said at least one metal silicide region, at least one parameter of at least one anneal process to be performed to form at least one metal silicide region on at least one subsequently processed substrate.

* * * * *